United States Patent [19]

Chen

[11] Patent Number: 5,494,817
[45] Date of Patent: Feb. 27, 1996

[54] SUGAR-BASED PROTEASE COMPOSITION FOR USE WITH CONSTANT-PH BORATE BUFFERS

[75] Inventor: Jie Chen, El Toro, Calif.

[73] Assignee: Allergan, Inc., Irvine, Calif.

[21] Appl. No.: 164,162

[22] Filed: Dec. 6, 1993

[51] Int. Cl.$^6$ .................................. C12N 9/96; C12N 9/48
[52] U.S. Cl. ..................... 435/188; 252/174.12; 435/212; 435/213; 435/219; 435/264; 435/222; 514/777
[58] Field of Search ........................ 252/174.12; 435/212, 435/188, 264, 213, 219, 222; 514/777

[56] References Cited

U.S. PATENT DOCUMENTS

| | | |
|---|---|---|
| Re. 32,672 | 5/1988 | Huth et al. . |
| 3,873,696 | 3/1975 | Randeri et al. . |
| 3,910,296 | 10/1975 | Karageozian et al. . |
| 4,039,662 | 8/1977 | Hecht et al. . |
| 4,048,122 | 9/1977 | Sibley et al. . |
| 4,076,845 | 2/1978 | Johannson ........................... 426/19 |
| 4,118,515 | 10/1978 | Rommele et al. ..................... 426/63 |
| 4,127,423 | 11/1978 | Rankin . |
| 4,201,706 | 5/1980 | Trager et al. . |
| 4,238,482 | 12/1980 | Peyman et al. . |
| 4,250,269 | 2/1981 | Buckman et al. . |
| 4,259,202 | 3/1981 | Tanaka et al. . |
| 4,264,155 | 4/1981 | Miyata . |
| 4,323,467 | 4/1982 | Fu . |
| 4,409,205 | 10/1983 | Shively . |
| 4,423,078 | 12/1983 | Darley et al. ........................ 426/20 |
| 4,443,432 | 4/1984 | Garabedian et al. . |
| 4,462,922 | 7/1984 | Boskamp ........................ 252/174.12 |
| 4,485,029 | 11/1984 | Kato et al. . |
| 4,500,441 | 2/1985 | Tanaka et al. . |
| 4,537,746 | 8/1985 | Ogunbiyi et al. . |
| 4,588,586 | 5/1986 | Kessler et al. . |
| 4,597,965 | 7/1986 | Holly . |
| 4,607,038 | 8/1986 | Ogata et al. . |
| 4,615,882 | 10/1986 | Stockel . |
| 4,620,979 | 11/1986 | Schachar . |
| 4,626,292 | 12/1986 | Sherman . |
| 4,642,234 | 2/1987 | Davies et al. . |
| 4,654,208 | 3/1987 | Stockel et al. . |
| 4,670,178 | 6/1987 | Huth et al. . |
| 4,690,773 | 9/1987 | Ogunbiyi et al. . |
| 4,731,192 | 3/1988 | Kenjo et al. . |
| 4,734,222 | 3/1988 | Winterton et al. . |
| 4,744,980 | 5/1988 | Holly . |
| 4,748,189 | 5/1988 | Su et al. . |
| 4,749,511 | 6/1988 | Lad et al. . |
| 4,758,595 | 7/1988 | Ogunbiyi et al. . |
| 4,808,239 | 2/1989 | Schafer et al. . |
| 4,829,088 | 5/1989 | Doulakas . |
| 4,836,986 | 6/1989 | Ogunbiyi et al. . |
| 4,863,627 | 9/1989 | Davies et al. . |
| 4,883,658 | 11/1989 | Holly . |
| 4,960,799 | 10/1990 | Nagy . |
| 4,978,535 | 12/1990 | Ractliff . |
| 5,011,661 | 4/1991 | Schäfer et al. . |
| 5,032,392 | 7/1991 | Varma . |
| 5,089,053 | 2/1992 | Chou et al. . |
| 5,116,868 | 5/1992 | Chen et al. . |
| 5,128,058 | 7/1992 | Ishii et al. . |
| 5,141,665 | 8/1992 | Sherman . |
| 5,169,455 | 12/1992 | Kessler . |

OTHER PUBLICATIONS

Lee et al J. Biol Chem vol. 256 No. 14 (Jul. 25, 1981).
APS Japan Abs of 62-36189 (Feb. 17, 1987) Torii et al Abs Published Jul. 18, 1987.
APS Japan Ab of 61-143316 (Jul. 1, 1986) Terazono Abstract Published Nov. 15, 1986.
Langenbucher, F; Langauer, T.; "Assessment of Powder Flowability by a Tiling-Drum Method", Pharmaceutical Development of Cibs-Geigy Ltd., Basel (Switzerland); 54, Nr. 9(1992); pp. 806-810.

*Primary Examiner*—Herbert J. Lilling
*Attorney, Agent, or Firm*—Jeffer, Mangels, Butler & Marmaro

[57] ABSTRACT

A composition for cleaning contact lenses includes a protease and a sugar in an amount effective to maintain substantially neutral pH in a borate buffer upon dissolution of the composition therein.

9 Claims, No Drawings

SUGAR-BASED PROTEASE COMPOSITION FOR USE WITH CONSTANT-PH BORATE BUFFERS

FIELD OF THE INVENTION

The present invention relates to a composition for use with eye care solutions. More specifically, the invention relates to a composition, including a protease, which is capable of maintaining a borate buffer solution at neutral pH.

BACKGROUND OF THE INVENTION

Enzymatic cleaning of contact lenses is known. For example, Kessler, U.S. Pat. No. 5,169,455, and Kessler et al., U.S. Pat. No. 4,558,586, disclose methods and compositions for cleaning and disinfecting contact lenses which include proteolytic enzymes. Ogunbiyi et al., U.S. Pat. No. 4,690,773, discloses an effervescent enzyme tablet for use in cleaning contact lenses.

Contact lens cleaning compositions, such as enzymatic compositions, particularly those in tablet form, can further include various binders and excipients. Kenjo et al., U.S. Pat. No. 4,731,192, teach chlorite-based contact lens cleaning systems which can include sugars, such as glucose, sucrose and fructose, as oxygen-consuming agents. Tanaka et al., U.S. Pat. Nos. 4,500,441 and 4,259,202, disclose various contact lens cleaning, storage and/or preservative compositions having non-ionic and anionic surfactants, or saccharose fatty acid esters, respectively, as active ingredients. The Tanaka compositions can include polysaccharides such as carboxymethylcellulose, dextran and agar to increase viscosity.

Lad et al., U.S. Pat. No. 4,749,511, disclose contact lens cleaning compositions including proteases in combination with endoproteinases, such as lys-C, together with binders and excipients such as dextran and carboxymethylcellulose.

Winterton et al., U.S. Pat. No. 4,734,222, disclose the use of sucrose in a contact lens cleaning composition. In the Winterton compositions, sucrose particles are used as abradants to physically remove lens soilants.

Since enzymatic activity is affected by the pH of the solution in which the cleaning is effected, it is frequently desirable to use a buffer, such as a neutral borate buffer, during enzymatic cleaning of contact lenses. For example, Huth, U.S. Pat. No. 4,670,178, teaches methods and compositions for cleaning and disinfecting contact lenses. The disclosed compositions can include an enzyme such as papain, together with a buffering agent such as sodium borate, and can be in tablet form. Lad et al. disclose contact lens cleaning compositions which optionally include a boric acid buffer system.

For effective enzymatic cleaning of contact lenses, the desired pH should be maintained throughout the cleaning process. Any excipients used in enzymatic cleaning compositions should not cause a significant drop in the pH of the buffer. Such excipients further should not have an adverse effect on the activity of other ingredients, such as anti-microbial agents, which may also be employed in the compositions. It would be desirable to provide such an enzymatic cleaning composition which is capable of maintaining the pH of a neutral borate buffer.

SUMMARY OF THE PREFERRED EMBODIMENTS

In accordance with one aspect of the present invention, there has been provided a composition comprising a protease, and a sugar in an amount effective to maintain substantially neutral pH in a borate buffer upon dissolution of the composition therein.

In a preferred embodiment, the sugar is sucrose, Di-Pac or a combination thereof. The composition preferably is in tablet form.

In accordance with another aspect of the present invention, a method of disinfecting contact lenses is provided. The method includes the steps of dissolving a composition as described above in a borate buffer, and immersing a contact lens in the buffer for a length of time effective to clean the lens, during which time the pH of the buffer remains substantially neutral.

In a preferred embodiment, the borate buffer includes a disinfecting agent. The sugar employed in the inventive composition does not cause a significant decrease in the anti-microbial activity of the disinfecting agent.

According to a further aspect of the invention, a method of maintaining a substantially constant pH in a neutral borate buffer is provided, comprising the step of adding to the buffer an amount of a sugar effective to maintain such pH.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

The sugars useful in compositions according to the present invention are capable of maintaining substantially neutral pH (i.e., about pH 7) in a conventional borate buffer. More specifically, the sugars do not cause a drop in pH of the neutral borate buffer of more than about 0.5 when the composition of the invention is dissolved in the buffer. Thus, "substantially neutral pH" does not deviate by more than about 0.5 from pH 7.

Preferred sugars include such sugars as sucrose, Di-Pac (a mixture of 97% sucrose and 3% maltodextrin, commercially available from Amstar Sugar Corporation and distributed by Austin Chemical Co., Illinois), D(+)-melizitose, L-L(−)-fucose, L-D(+)-melibiose, agar, agarose, and combinations thereof. Di-Pac is particularly preferred. It is believed that these cyclic sugars do not form complexes with borate ion in solution, i.e., do not titrate the borate ions, and thus do not significantly reduce the pH of the buffer. Non-cyclic cis-diol sugars, however, are not preferred; it is believed that these sugars are capable of forming complexes with borate ions. Carboxymethylcellulose and dextran are also preferably not included in the inventive compositions.

In addition to having the required pH-maintenance function, sugars within the invention preferably also are "flowable." That is, the sugars remain in a granular state and are easily poured, exhibiting at most a limited tendency to agglomerate together. Flowability of sugars can be measured by a number of techniques known to those of skill in the art, for example in the method of Langenbucher et al., *Pharm. Ind.* 54:806–810 (9) (1992). For purposes of the present invention, a sugar is "flowable" if it is characterized by a wedge angle $\Delta_x$, as defined in Langenbucher et al., of less than 10°.

The drop in pH of the neutral borate buffer to which a composition according to the invention is added will depend on the buffering capacity of the buffer, and also on the amount of sugar in the composition. Thus, an upper limit on the amount of sugar in a composition of the invention for use with a given borate buffer can be determined by adding specific quantities of the sugar to a standard amount of the buffer, such as 10 ml, and observing the point at which the drop in pH of the buffer equals 0.5.

Typically, a composition according to the invention will comprise about 30% to 90% by weight, preferably 50% to 90% by weight, of the sugar or combination of sugars. More or less than the typical amount can be used as long as the pH of the borate buffer to which the composition is added is maintained neutral, i.e., does not drop by more than about 0.5.

The protease employed in accordance with the invention may be selected from those enzymes which are conventionally employed in the enzymatic cleaning of contact lenses. For example, many of the enzymes disclosed in Huth et al., Reissue U.S. Pat. No. 32,672 and Karageozian et al., U.S. Pat. No. 3,910,296 are useful in the present invention. These patents are incorporated in their entirety by reference herein.

A preferred group of proteases are the derived alkaline proteases generically called subtilisin enzymes. Reference is made to Keay, L., Moser, P. W. and Wildi, B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases from Bacillus Species," Biochemical and Biophysical Research Comm,, Vol. 34, No. 5, pp. 600–604 (1969).

The subtilisin enzymes are broken down into two subclasses, subtilisin A and subtilisin B. In the subtilisin A grouping are enzymes derived from such species as *B. subtilis, B. licheniformis* and *B. pumilis*. Organisms in this sub-class produce little or no neutral protease or amylase. The subtilisin B sub-class is made up of enzymes from such organisms as *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, chymotrypsin, pepsin, streptokinase, streptodornase, ficin, carboxypeptidase, collagenase, keratinase, carboxylase, aminopeptidase, elastase, chymopapain, bromelin, aspergillo-peptidase A and B, pronase E (from *S. griseus*) and dispase (from *Bacillus polymyxa*). However, endoproteinases, such as endoproteinase lys-C, preferably are not included in the inventive compositions.

An effective amount of enzyme is to be used in the practice of this aspect of the present invention. An effective amount is that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme.

As a basic yardstick, the working solution should contain sufficient enzyme to provide about 0.001 to about 3 Anson units of activity, preferably about 0.01 to about 1 Anson unit, per single lens treatment. Higher or lower amounts may be used. Appropriate amounts are readily determined by the skilled artisan through routine testing.

Since, as noted, enzyme activity is pH dependent, the enzyme selected for use in a composition according to the invention should be effective at neutral pH.

Additional components may be incorporated into a composition according to the invention, provided the combined effect of all of the ingredients does not result in a drop in pH of the borate buffer greater than about 0.5. For example, components such as effervescing agents, stabilizers, chelating and/or sequestering agents, coloring agents, tonicity adjusting agents, surfactants, binders, lubricants, carriers, and other excipients normally used in producing tablets, powders, etc. may be so employed.

Examples of suitable effervescing agents include, but are not limited to, tartaric or citric acid used in combination with a suitable alkali metal salt such as sodium carbonate.

Examples of preferred chelating agents include ethylenediaminetetraacetic acid (EDTA) and its salts (disodium) which are normally employed in amounts from about 0.025 to about 2.0% (w/v) in the buffer solution.

The binders and lubricants for tableting purposes and other excipients normally used for producing tablets, powders and the like, may be incorporated into compositions within the present invention. Preferably the composition is in tablet form, although, e.g., powdered or granulated compositions, or even liquid compositions, could also be used.

The borate buffer to which a composition according to the invention is added preferably includes a disinfecting or preserving agent. Such agents include without limitation biguanides, polyquats including Croquats (available from Croda, Inc.), chlorhexidine, Miramine, Dymed, Purogene, water soluble cationic polymers (WSCPs, available from Buckman Laboratories, Inc. and described in U.S. Pat. No. 4,250,269, which is incorporated herein by reference)including poly [oxyethylene (dimethyliminio) ethlylene-(dimethyliminio) ethylene dichloride] ("WSCP(1)"), $H_2O_2$, $ClO_2$, antibiotics and any other disinfecting agent which is compatible with a neutral borate buffer. The anti-microbial activity of such agents is not adversely affected by the sugars included in the inventive compositions. The buffer can further include detoxifying agents as appropriate for use with particular disinfecting agents.

The invention is illustrated in more detail by the following non-limiting exemplary tablet compositions.

EXAMPLE 1

| | |
|---|---|
| Di-Pac | 40.0 mg |
| Subtilisin | 0.003 Anson unit (Au) |
| Polyethylene glycol 3350 | 4.0 mg |
| PVP K-30 | 4.0 mg |

EXAMPLE 2

| | |
|---|---|
| Di-Pac | 40.0 mg |
| Papain | 0.003 Au |
| L-Cysteine HCl | 15. mg |
| Polyethylene glycol 3350 | 4.0 mg |
| PVP K-30 | 4.0 mg |

-continued

|                    |        |
|--------------------|--------|
| Tartaric acid      | 10. mg |
| Sodium carbonate   | 20. mg |

EXAMPLE 3

|                         |          |
|-------------------------|----------|
| Sucrose                 | 40.0 mg  |
| Trypsin                 | 0.003 Au |
| Polyethylene glycol 3350| 4.0 mg   |
| PVP K-30                | 4.0 mg   |
| Tartaric acid           | 10. mg   |
| Sodium carbonate        | 10. mg   |

EXAMPLE 4

|                         |          |
|-------------------------|----------|
| Sucrose                 | 40.0 mg  |
| Bromelin                | 0.003 Au |
| Polyethylene glycol 3350| 4.0 mg   |
| PVP K-30                | 4.0 mg   |
| Tartaric acid           | 10. mg   |
| Sodium carbonate        | 10. mg   |

The following exemplary contact lens cleaning methods illustrate the use of compositions according to the invention. In each case, all percentages are in weight/volume:

EXAMPLE 5

A tablet composition of Example 1, above, is dissolved in 2 ml of a borate buffer having the following composition (all percentages are weight/volume):

|                 |         |
|-----------------|---------|
| Sodium chloride | 0.85%   |
| Boric acid      | 1.0%    |
| Sodium borate   | 0.4%    |
| Miramine        | 0.0014% |

A contact lens is placed in the resulting solution for 4 hr, after which time the lens is cleaned and disinfected. The pH of the solution is not observed to substantially decrease. The lens is then rinsed and inserted into the eye of the user.

EXAMPLE 6

A tablet composition of Example 1, above, is dissolved in 2 ml of a borate buffer having the following composition:

|                  |        |
|------------------|--------|
| Sodium chloride  | 0.67%  |
| Boric acid       | 0.39%  |
| Sodium borate    | 0.20%  |
| Disodium EDTA    | 0.13%  |
| Croquat          | 0.001% |
| WSCP             | 0.006% |

A contact lens is placed in the resulting solution for 4 hr, after which time the lens is cleaned and disinfected. The pH of the solution is not observed to substantially decrease.

EXAMPLE 7

A tablet composition of Example 1, above, is dissolved in 2 ml of a borate buffer having the following composition:

|                 |       |
|-----------------|-------|
| Sodium chloride | 0.37% |
| Boric acid      | 0.60% |
| Sodium borate           | 0.20%   |
| Sodium EDTA             | 0.05%   |
| Tyloxapol               | 0.025%  |
| Polyhexamethylene biguanide | 0.0001% |

A contact lens is placed in the resulting solution for 4 hr, after which time the lens is cleaned and disinfected. The pH of the solution is not observed to substantially decrease.

EXAMPLE 8

A tablet composition of Example 1, above, is dissolved in 2 ml of a borate buffer having the following composition:

|                 |       |
|-----------------|-------|
| Sodium chloride | 0.85% |
| Boric acid      | 1.00% |
| Sodium borate   | 0.40% |

A contact lens is placed in the resulting solution, then subjected to one cycle (approximately 1 hr) of a standard heat disinfection process, after which time the lens is cleaned and disinfected. The pH of the solution is not observed to substantially decrease.

EXAMPLE 9

A delayed-release tablet composition is prepared:

a) core tablet

|                                 |          |
|---------------------------------|----------|
| Di-Pac                          | 30.0 mg  |
| Subtilisin A                    | 0.15 Au  |
| N-Acetyl cysteine (coarse granular) | 15.0 mg  |
| Sodium carbonate (anhydrous)    | 20.0 mg  |
| Polyethylene glycol 3350        | 2.0 mg   | b) coating solution

One of the following coating solutions is employed:

|      |                         |         |
|------|-------------------------|---------|
| I.   | Methocel ®              | 3.37%   |
|      | Polyethylene glycol 300 | 0.67%   |
|      | Isopropyl alcohol       | 18.48%  |
|      | Water (purified)        | 77.48%  |
| II.  | Eudragit ® L 100        | 6.25%   |
|      | Triethyl citrate        | 0.47%   |
|      | Isopropyl alcohol       | 93.28%  |

Methocel® is a hydroxypropyl methylcellulose polymer sold by Dow Chemical Co. Eudragit® L 100 is a methyl acrylate/methacrylic acid copolymer sold by Rohm Pharma.

Either coating solution (I or II) is sprayed onto the core tablet using conventional equipment, e.g., a film coating pan. An appropriate amount of coating material is applied to the core tablet to produce the coated tablet. This amount can readily be determined through routine testing. The appropriate amount of coating (preferably 5 to 10 mg per tablet) effectively delays the release of the core tablet into a disinfecting solution, e.g., a solution containing chlorine dioxide, for a sufficient time to allow appropriate disinfection.

A 10 ml sample of a borate buffer having the following composition is prepared:

|                 |         |
|-----------------|---------|
| Purogene ®      | 0.015%  |
| Sodium chloride | 0.730%  |

| | |
|---|---|
| Boric acid | 0.200% |
| Hydrochloric acid | 7.15 to 7.25 pH |
| Sodium Hydroxide | 7.15 to 7.25 pH |
| Water (purified) | q.s. |

Purogene® is a stabilized chlorine dioxide product containing 2.0% by weight of potential chlorine dioxide and 0.085% by weight of sodium carbonate, and is sold by Bio-cide International, Inc.

The sample is placed in a plastic container containing a plastic disk which contains platinum, as platinum oxide. The platinum activates chlorine dioxide, producing 1 to 2 ppm chlorine dioxide in the 10 ml solution.

A contact lens is placed in the resulting solution. After 30 min, the lens is disinfected and the enzyme in the coated core is released to the solution. The contact lens is subsequently maintained in the solution for 4 hr, after which time the lens is cleaned as well as disinfected. The pH of the solution is not observed to substantially decrease during the cleaning process.

It is contemplated that applications of the inventive method for maintaining substantially neutral pH in a borate buffer will not be limited to ophthalmic applications, such as eye care products. Rather, the inventive method will be broadly applicable in any situation in which maintenance of substantial pH neutrality for enzyme activity in a borate buffer is desired. Such applications include without limitation surgical applications such as wound irrigation; intravenous administration of drugs and/or nutriments; systemic release of pharmaceutically useful compounds, etc.

What is claimed is:

1. A solid composition consisting essentially of
   (a) a protease, and
   (b) a cyclic sugar which will not cause a drop of more than about 0.5 in the pH of a neutral borate buffer;
   wherein the sugar is present in the composition in an amount effective to maintain substantially neutral pH in a borate buffer upon dissolution of said composition therein.

2. A composition as claimed in claim 1, wherein said sugar is present in an amount from about 30 to 90 wt %.

3. A composition as claimed in claim 2, wherein said sugar is present in an amount from about 50 to 90 wt %.

4. A cyclic composition as claimed in claim 1, wherein said sugar is flowable.

5. A composition as claimed in claim 1, wherein said sugar is selected from the group consisting of sucrose, a mixture of 97% sucrose and 3% maltodextrin, D(+)-melizitose, L-L(−)-fucose, L-D(+)-melibiose, agar, agarose, and combinations thereof.

6. A composition as claimed in claim 1, wherein said sugar does not comprise dextran or carboxymethylcellulose.

7. A composition as claimed in claim 1, wherein said protease is selected from the group consisting of subtilisin, papain, trypsin, bromelin, ficin and pancreatin.

8. A composition as claimed in claim 1, wherein said protease does not comprise an endoproteinase.

9. A composition as claimed in claim 1 in tablet form.

* * * * *